United States Patent [19]

Schmierer et al.

[11] Patent Number: 4,623,380
[45] Date of Patent: Nov. 18, 1986

[54] ISOINDOLES, PROCESSES FOR THEIR PREPARATION AND THEIR USE AS HERBICIDAL AGENTS

[75] Inventors: Roland Schmierer, Todtenweis; Reinhard Handte, Gablingen; Hilmar Mildenberger, Kelkheim; Klaus Bauer, Rodgau; Hermann Bieringer, Eppstein; Helmut Bürstell, Frankfurt am Main, all of Fed. Rep. of Germany

[73] Assignee: Hoechst Aktiengesellschaft, Frankfurt am Main, Fed. Rep. of Germany

[21] Appl. No.: 697,506

[22] Filed: Feb. 1, 1985

[30] Foreign Application Priority Data

Feb. 3, 1984 [DE] Fed. Rep. of Germany ....... 3403730

[51] Int. Cl.$^4$ ................... A01N 43/48; C07D 471/14; C07D 401/14
[52] U.S. Cl. ......................................... 71/92; 546/65; 546/18; 546/70; 546/82; 544/126; 544/361; 544/125
[58] Field of Search .............. 546/82; 71/92; 544/361, 544/126

[56] References Cited

FOREIGN PATENT DOCUMENTS 0041623 12/1981 European Pat. Off. .............. 546/82

Primary Examiner—Henry R. Jiles
Assistant Examiner—J. Richter
Attorney, Agent, or Firm—Curtis, Morris & Safford

[57] ABSTRACT

Compounds of the formula

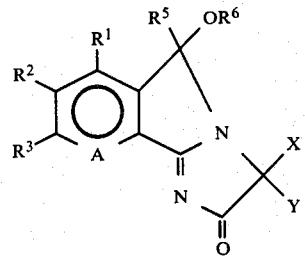

in which A denotes $C-R^4$ or N; X denotes alkyl and Y denotes alkyl, cycloalkyl, alkenyl, alkynyl, phenyl or benzoyl, or, together with X, cycloalkyl; $R^1$–$R^4$ denote H, alkyl, alkoxy, alkoxycarbonyl, halogen, $NO_2$, CN, phenoxy or (substituted) phenyl; $R^5$ denotes H or alkyl; and $R^6$ denotes H, (substituted) alkyl, halogenoalkenyl, cycloalk(en)yl, alkynyl, (substituted) phenyl or carboxylic acid ester, carboxylic acid amide, sulfo-ester or acyl radicals, are effective plant treatment agents, in particular herbicides.

9 Claims, No Drawings

ISOINDOLES, PROCESSES FOR THEIR PREPARATION AND THEIR USE AS HERBICIDAL AGENTS

Imidazolodiones and imidazolo-pyrrolo-pyridinediones with a herbicidal activity are already known from German Offenlegungsschriften 2,700,270 and 3,121,736.

The present invention relates to isoindole compounds of the formula I

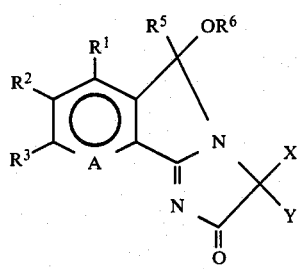

in which

A denotes C-$R^4$ or N;

X denotes $C_1$-$C_4$-alkyl; and

Y denotes $C_1$-$C_6$-alkyl, $C_3$-$C_6$-cycloalkyl, $C_2$-$C_4$-alkenyl, $C_2$-$C_4$-alkynyl, phenyl or benzyl; or X and Y, together with the carbon atom to which they are bonded, denote a $C_3$-$C_6$-spirocycloalkyl group which is optionally substituted by —$CH_3$;

$R^1$, $R^2$, $R^3$ and $R^4$ independently of one another denote hydrogen, $C_1$-$C_4$-alkyl, $C_1$-$C_6$-alkoxy, $C_1$-$C_6$-alkoxycarbonyl, halogen, nitro, cyano, phenoxy or phenyl, which is optionally substituted by $C_1$-$C_4$-alkyl, $C_1$-$C_4$-alkoxy or halogen, it being possible for in each case two radicals $R_1$, $R_2$, $R_3$ or $R_4$ in the ortho-position relative to one another together to form the grouping —CH═CH—CH═CH—; or the radicals denote ($C_1$-$C_2$)-halogenoalkyl, in particular $CF_3$;

$R^5$ denotes hydrogen or $C_1$-$C_4$-alkyl;

$R^6$ denotes hydrogen, $C_1$-$C_{12}$-alkyl, which is optionally mono- or di-substituted, but preferably monosubstituted, by $C_1$-$C_4$-alkoxy, ($C_1$-$C_4$)alkoxyethoxy, $C_3$-$C_6$-cycloalkyl, benzyloxy, phenyl, tolyl, halogenophenyl, halogen, cyano, hydroxyl, ($C_1$-$C_4$)-alkoxycarbonyl, oxiranyl, tetrahydrofuryl, ($C_1$-$C_4$)-alkylamino, ($C_1$-$C_4$)-dialkylamino, $C_1$-$C_4$-alkylthio, triazolyl, imidazolyl or the grouping

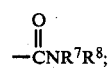

or denotes $C_3$-$C_6$-alkenyl, $C_3$-$C_6$-alkadienyl, $C_3$-$C_6$-halogenoalkenyl, $C_3$-$C_6$-cycloalkyl, $C_5$- or $C_6$-cycloalkenyl or $C_3$-$C_6$-alkynyl; or denotes phenyl, which can optionally be substituted by up to two $C_1$-$C_4$-alkyl, nitro, $C_1$-$C_4$-alkoxycarbonyl, halogen or methoxy groups; or denotes $C_1$-$C_6$-alkoxycarbonyl, phenoxycarbonyl, halogenophenoxycarbonyl, $C_1$-$C_4$-alkylsulfonyl, trihalogenomethylsulfonyl, benzenesulfonyl, halogenobenzenesulfonyl, toluenesulfonyl or the grouping

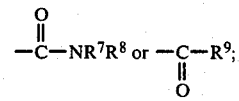

$R^7$ denotes hydrogen or $C_1$-$C_4$-alkyl; and $R^8$ denotes hydrogen, $C_1$-$C_6$-alkyl, $C_3$-$C_6$-alkenyl, phenyl, halogenophenyl or methylphenyl; or $R_7$ and $R_8$, together with the nitrogen atom, denote a 5-membered or 6-membered ring in which one carbon atom can be replaced by oxygen or nitrogen and which is optionally substituted by up to two methyl groups; and $R^9$ denotes ($C_1$-$C_{12}$)-alkyl, optionally mono-, di-or tri-substituted by fluorine, chlorine and bromine and/or monosubstituted by ($C_1$-$C_4$)-alkoxy, ($C_1$-$C_4$)-alkoxycarbonyl, ($C_1$-$C_4$)-alkylthio, phenyl or phenoxy, it being possible for the latter two to be optionally mono-, di- or tri-substituted by halogen, ($C_1$-$C_4$)-alkyl, $NO_2$, $CF_3$ or ($C_1$-$C_4$)-alkoxy; or denotes ($C_2$-$C_6$)-alkenyl, ($C_3$-$C_6$)halogenoalkenyl, ($C_3$-$C_6$)-alkynyl or phenyl, which can be mono- or di-substituted by F, Cl, Br, $CF_3$, ($C_1$-$C_4$)alkyl and/or ($C_1$-$C_4$)alkoxy, and optical isomers thereof and (if A represents N) their acid addition salts and N-oxides.

If —$NR^7R^8$ represents a heterocyclic ring, it is preferably a pyrrolidine, piperidine, morpholine or N-methylpiperazine ring.

The compounds according to the invention are obtained by a process which comprises—if $R^5$=hydrogen (a) partially reducing compounds of the general formula II

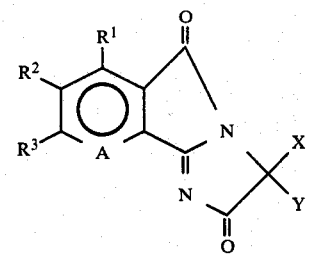

(b) hydrolyzing the dichloromethyl compounds of the formula III

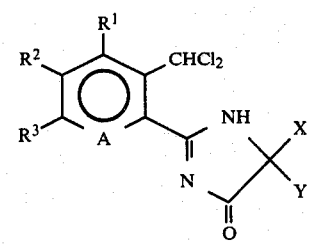

or (c) hydrolyzing and cyclizing, with the detachment of water, the dichloromethyl compounds of the formula IV

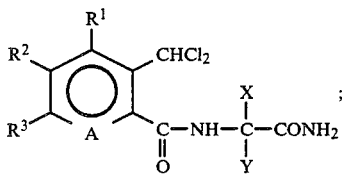

or—for $R^5 = C_1-C_4$-alkyl -

(d) reacting compounds of the general formula II with organometallic alkyl compounds; or—for $R^5$=hydrogen or $C_1-C_4$-alkyl -

(e) condensing compounds of the formula V

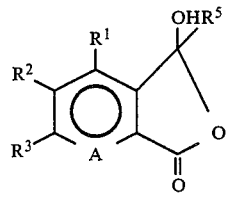

with the aminoamides of the formula VI

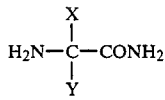

with cyclization, and, if desired, converting the resulting compounds of the formula I with $R^6$=hydrogen into other compounds of the formula I by alkylation, acylation, sulfonation, carbamyolation, salt formation or oxidation.

Re (a): The compounds II are known from German Offenlegungsschriften 3,121,736 and 2,700,270. Examples of compounds which are suitable for the reduction are complex metal hydrides, such as sodium borohydride or deactivated lithium alanate (c.f., for example, Chem. Lett. 1983, 385–8).

In a preferred process, the reduction is carried out with sodium borohydride in alcohols or ethers, such as ethanol, tetrahydrofuran or diethylene glycol dimethyl ether, at temperatures from −10° C. to +80° C., advantageously between 0° and +50° C. Further reaction of the isoindole derivatives to give the o-hydroxymethyl compound, as is described in German Offenlegungsschrift 3,121,736, surprisingly does not occur under the above reaction conditions.

Re (b): The preparation of the dichloromethyl compounds is described in German Patent Application P 33 40 595.6. The hydrolysis is carried out by reaction with aqueous solutions of alkali metal or alkaline earth metal hydroxides or carbonates, such as sodium hydroxide, potassium hydroxide or sodium carbonate, at temperatures from about 20° C. to 150° C., if appropriate under pressure. Inert organic solvents, such as toluene, chloroform, ethanol or higher-boiling ethers, can be added to the reaction mixture. The hydrolysis proceeds surprisingly easily and without the decomposition of the imidazolinone ring which otherwise takes place under the conditions for hydrolysis of o-substituted dichloromethyl compounds being observed.

Re (c): The preparation of the compounds IV is likewise described in German Patent Application P 33 40595.6. The compounds are hydrolyzed under the conditions described in (b). The cyclization, which proceeds with the detachment of water, to the tricyclic system can already occur during the hydrolysis.

Re (d): The reaction of the compounds II with molar amounts of organometallic alkyl compounds, such as lithium-alkyl derivatives or, advantageously, Grignard derivatives, is preferably carried out at temperatures from −40° C. to +40° C. in solvents such as diethyl ether, ethylene glycol dimethyl ether and tetrahydrofuran.

Re (e): The aminoamides VI are known from German Offenlegungsschrift 2,700,270, and the o-carbonylcarboxylic acids V are known, for example, from Beilstein E III, 10, 3025. The latter are formed by tautomerization from corresponding aldehyde acids:

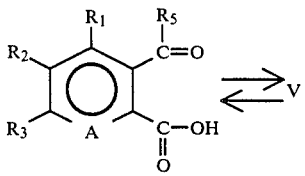

The condensation of VI with V is carried out with simultaneous removal of water, advantageously in the presence of acid catalysts, such as p-toluenesulfonic acid, at temperatures from about 0° C. to 150° C. The water formed is advantageously separated off by azeotropic distillation with a solvent such as toluene or xylene.

If $R^1 \neq R^4$ and/or $R^2 \neq R^3$, the starting substances of the formulae II and V can occur, on the basis of the synthesis routes which lead to them, in two position isomer forms in which the substituents $R^1$ and $R^4$ and/or $R^2$ and $R^3$ have changed places. The compounds of the formula I prepared from these compounds can therefore also exhibit the same position isomerism, so that mixtures of the particular position isomers may be present.

The reaction products of the formula I where $R^6$=hydrogen can be converted into the other compounds of the formula I in a simple manner which is known per se, by reaction with alkylating agents (methyl iodide or methyl bromoacetate) or acylating agents (acid chlorides or toluenesulfonyl chloride) in the presence of bases, with isocyanates or by oxidation, for example with $H_2O_2$.

The compounds of the formula I according to the invention ($R^6$=hydrogen) are exclusively present in the cyclic hemi-aminal form shown.

The present compounds according to the invention exhibit an excellent herbicidal activity against a broad spectrum of economically important monocotyledon and dicotyledon harmful plants. The active ingredients have a good effect even on perennial root-propagated weeds which are difficult to combat. It is irrelevant here whether the substances are applied by pre-sowing, pre-emergence or post-emergence spraying. If the compounds according to the invention are applied to the surface of the soil before germination, emergence of the seedlings is not completely prevented. The weeds grow to the cotyledon stage, but their growth then stops and, finally, they die completely after three weeks.

When the active ingredients are applied to the green parts of plants by the post-emergence method, a drastic stop in growth likewise occurs very rapidly after the treatment, and the weeds remain in the growth stage in which they were present at the time of application, or, after a certain period, die completely, so that weed competition which is harmful to the crop plants can in this manner be eliminated very early and in a lasting manner by using the novel agents according to the invention. Although the compounds according to the invention exhibit an excellent herbicidal activity against monocotyledon and dicotyledon weeds, damage to plants of economically important crops, such as, for example, wheat, barley, rye, rice, corn, sugar beet, cotton and soybean, is only insignificant or non-existent. Compared with the prior art, the present substances according to the invention therefore have a considerably improved selectivity in crop plants. For these reasons, the present compounds are particularly suitable for combating undesirable plant growth in agricultural plantations of useful crops.

Moreover, they exhibit growth-regulating properties in crop plants. They have a regulating effect on the endogenous metabolism of the plant and can therefore be used to facilitate harvesting, such as, for example, by triggering off desiccation, abscission and growth compression. They are moreover suitable for general control and inhibition of undesirable vegetative growth, without thereby destroying the plants. Inhibition of vegetative growth is of great importance in many monocotyledon and dicotyledon crops, since lodging can thereby be reduced or completely prevented.

The agents according to the invention can be applied as wettable powders, emulsifiable concentrates, solutions which can be sprayed, dusts, dressing agents, dispersions, granules or microgranules in the customary formulations.

Wettable powders are products which are uniformly dispersible in water and which, in addition to the active ingredient, and if appropriate apart from a diluent or inert substance, also contain wetting agents, for example polyoxyethylated alkylphenols, polyoxyethylated fatty alcohols or alkyl- or alkylphenyl-sulfonates, and dispersing agents, for example sodium lignin-sulfonate, sodium 2,2'-dinaphthylmethane-6,6'-disulfonate, sodium dibutylnaphthalenesulfonate or sodium oleylmethyltauride. The powders are prepared in the customary manner, for example by grinding and mixing the components.

Emulsifiable concentrates can be prepared, for example, by dissolving the active ingregient in an inert organic solvent, for example butanol, cyclohexanone, dimethylformamide, xylene or higher-boiling aromatics or hydrocarbons, with the addition of one or more emulsifiers. In the case of liquid active ingredients, all or some of the solvent content can also be omitted. Examples of emulsifiers which can be used are: calcium alkylarylsulfonates, such as Ca dodecylbenzenesulfonate, or non-ionic emulsifiers, such as fatty acid polyglycol esters, alkyl-aryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusts can be obtained by grinding the active ingredient with finely divided, solid substances, for example talc or natural clays, such as kaolin, bentonite, pyrophillite or diatomaceous earth.

Granules can be prepared either by spraying the active ingredient onto an adsorbent, granular inert material or by applying active ingredient concentrations to the surface of carriers, such as sand or kaolinites, or of granular inert material, by means of binders, for example polyvinyl alcohol, sodium polyacrylate or mineral oils. It is also possible to granulate suitable active ingredients in the customary manner for the preparation of fertilizer granules, if desired as a mixture with fertilizers.

The active ingredient concentration in wettable powders is, for example, about 10 to 90% by weight, the remainder to make up to 100% by weight consisting of the usual formulation constituents. The active ingredient concentration in emulsifiable concentrates can be about 5 to 80% by weight. Dust-like formulations usually contain 5 to 20% by weight of active ingredient, and solutions which can be sprayed contain about 2 to 20% by weight. The active ingredient content in granules depends partly on whether the active compound is in liquid or solid form and on what granulation auxiliaries, fillers and the like are used.

In addition, the active ingredient formulations mentioned contain, if appropriate, the particular customary tackifying agents, wetting agents, dispersing agents, emulsifiers, penetration agents, solvents, fillers or excipients.

For application, the concentrates in the commercially available form are diluted, if appropriate, in the customary manner, for example by means of water in the case of wettable powders, emulsifiable concentrates, dispersions and sometimes also microgranules. Dust-like and granular formulations and solutions which can be sprayed are usually not diluted further with additional inert substances before application.

The application amount required varies according to the external conditions, such as temperature, humidity and the like. It can vary within wide limits, for example between 0.005 and 10.0 kg/ha or more of active substance, but is preferably between 0.01 and 5 kg/ha.

Mixtures or mixed formulations with other active ingredients, such as, for example, insecticides, acaricides, herbicides, fertilizers, growth regulators or fungicides, are also possible, if appropriate.

Some formulation examples may be mentioned in the following:

A dust is obtained by mixing 10 parts by weight of active ingredient and 90 parts by weight of talc or inert substance and comminuting the mixture in an impact mill.

A wettable powder which is easily dispersible in water is obtained by mixing 25 parts by weight of active ingredient, 64 parts by weight of kaolin-containing quartz, as an inert substance, 10 parts by weight of potassium lignin-sulfonate and 1 part by weight of sodium oleylmethyltauride, as a wetting and dispersing agent, and grinding the mixture in a pinned disk mill.

A dispersion concentrate which is easily dispersible in water is obtained by mixing 20 parts by weight of active ingredient with 6 parts by weight of alkylphenol polyglycol ether (Triton X 207), 3 parts by weight of isotridecanol polyglycol ether (8 moles of ethylene oxide) and 71 parts by weight of paraffinic mineral oil (boiling range, for example, about 255° to above 377° C.) and grinding the mixture to a fineness of less than 5 microns.

An emulsifiable concentrate is obtained from 15 parts by weight of active ingredient, 75 parts by weight of cyclohexanone, as the solvent, and 10 parts by weight of oxyethylated nonylphenol (10 moles of ethylene oxide), as the emulsifier.

The following examples serve to further illustrate the invention:

A. PREPARATION EXAMPLES

Example 1

2,3a-Dihydro-4-hydroxy-3-isopropyl-3-methyl-2-oxo-[5H]imidazolo[1,2b][1H]isoindole 22.8 g (0.076 mole) of 2-(2-dichloromethylphenyl)-5-isopropyl-5-methyl-4-oxo-2-imidazoline are heated at 90° C. with 6.4 g (0.16 mole) of sodium hydroxide in 150 ml of water for 2 hours, the mixture is cooled and the product is filtered off with suction. After drying in vacuo, 10.5 g (56% of theory) of 2,3a-dihydro-4-hydroxy-3-isopropyl-3-methyl-2-oxo-[5H]imidazolo[1,2b][1H]isoindole remain as a slightly pale yellow solid of melting point 233°–234° C.

Example 2

2,3a-Dihydro-3-isopropyl-4-methoxy-3-methyl-4-oxo-[5H]imidazolo[1,2b][1H]isoindole 10 g (0.041 mole) of 2,3a-dihydro-4-hydroxy-3-isopropyl-3-methyl-2-oxo-[5H]imidazolo[1,2b][1H]isoindole are dissolved in 50 ml of absolute dimethylformamide, and 1.35 g (0.045 mole) of 80% strength sodium hydride are added at room temperature. When the evolution of gas has ended, 6.7 g (0.049 mole) of methyl iodide are added, the mixture is subsequently stirred at room temperature for 1 hour and the reaction mixture is taken up in toluene, washed twice with water, dried and evaporated to give 9.4 g (89% of theory) of 2,3a-dihydro-3-isopropyl-4-methoxy-3-methyl-4-oxo-[5H]imidazolo[1,2b][1H]isoindole as a colorless oil.

$^1$H-NMR (60 MHz, CDCl$_3$) $\delta$ = 1.00, 1.18 (2d, J = 7 Hz, in each case 3H, —CH(C$\underline{H}$$_3$)$_2$); 1.67 (s, 3H, CH$_3$); 2.13 (h, J = 7 Hz, 1H, —C$\underline{H}$-(CH$_3$)$_2$); 3.18 (s, 3H, OCH$_3$) 5.65 (s, 1H, CH-O); and $\overline{7.5}$–8.0 ppm (m, 4H, phenyl).

Example 3

4-Benzoyloxy-2,3a-dihydro-3-isopropyl-3-methyl-2-oxo[5H]imidazolo[1,2b][1H]isoindole Analogously to Example 2, 6.8 g (0.049 mole) of benzoyl chloride were added to the corresponding amount of sodium salt. Analogous working up gives 12.7 g (89% of theory) of 4-benzoyloxy-2,3a-dihydro-3-isopropyl-3-methyl-2-oxo-[5H]-imidazolo[1,2b][1-H]isoindole as a yellow oil.

$^1$H-NMR (60 MHz, CDCl$_3$) $\delta$ = 1.07, 1.18 (d, J = 7 Hz, in each case 3H, —CH(C$\underline{H}$$_3$)$_2$); 1.82 (s, 3H, CH$_3$); 2.13 (h, J = 7 Hz, 1H, —C$\underline{H}$(CH$_3$)$_2$); 6.60 (s, 1H, —CHO); and 7.2–8.2 ppm (9$\overline{H}$, phenyl).

Example 4

2,3a-Dihydro-4-N-methyl-carbamoyloxy-3-isopropyl-3-methyl-2-oxo-[5H]-imidazolo[1,2b][1H]isoindole 8 g (0.033 mole) of 2,3a-dihydro-4-hydroxy-3-isopropyl-3-methyl-2-oxo-[5H]imidazolo[1,2b][1H]isoindole are stirred with 2.25 g (0.04 mole) of methyl isocyanate in 50 ml of absolute acetonitrile at room temperature for 1 hour. The mixture is taken up in 100 ml of toluene, washed twice with water and dried over sodium sulfate. Concentration gives 7.5 g (80% of theory) of 2,3a-dihydro-4-N-methyl-carbamyloxy-3-isopropyl-3-methyl-2-oxo[5H]-imidazolo[1,2b][1H]isoindole as a colorless oil.

$^1$H-NMR (60 MHz, CDCl$_3$) $\delta$ = 1.07, 1.17 (2d, J = 7 Hz, in each case 3H, CH(C$\underline{H}$$_3$)$_2$); 1.73 (s, 3H, CH$_3$); 2.13 (h, J = 7 Hz, C$\underline{H}$(CH$_3$)$_2$); $\overline{2.90}$, 3.00 (2s, together 3H, NCH$_3$); 6.33 (s, $\overline{1H}$, CHO); and 7.4–8.3 (m, 5H, NH, phenyl) ppm.

The examples in Table 1 are prepared in an analogous manner.

TABLE 1

Compounds of the general formula I

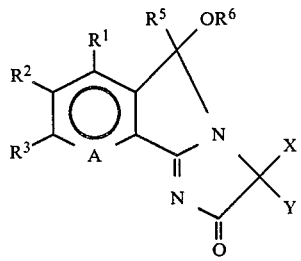

| Example No. | R$^1$ | R$^2$ | R$^3$ | A | R$^4$ | R$^5$ | R$^6$ | X | Y | Melting Point [°C.] |
|---|---|---|---|---|---|---|---|---|---|---|
| 5 | H | H | H | C—R$^4$ | H | H | H | C$_2$H$_5$ | C$_2$H$_5$ | 152–4 |
| 6 | " | " | " | " | " | " | —CH$_2$—CH$_2$—Br | " | " | " |
| 7 | " | " | " | " | " | " | —CH$_2$—CH$_2$—O—C$_2$H$_5$ | " | " | Oil |
| 8$^2$ | " | " | CH$_3$ | " | " | " | —CH$_3$ | CH$_3$ | " | " |
| 9$^2$ | " | " | " | " | " | " | —C(O)—C$_6$H$_3$Cl$_2$ | " | CH$_3$ | " |
| 10 | " | " | H | " | " | " | —C$_2$H$_5$ | " | CH(CH$_3$)$_2$ | " |
| 11 | " | " | " | " | " | " | —CH(CH$_3$)$_2$ | " | " | " |
| 12 | " | " | " | " | " | " | —n-C$_6$H$_{13}$ | " | " | " |
| 13 | " | " | " | " | " | " | —CH$_2$—CH=CH$_2$ | " | " | 96–8 |
| 14$^1$ | " | " | " | " | " | " | —CH=C=CH$_2$ | " | " | Oil |
| 15 | " | " | " | " | " | " | —CH$_2$—C≡CH | " | " | 90–1 |

TABLE 1-continued

Compounds of the general formula I

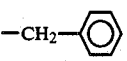

| Example No. | $R^1$ | $R^2$ | $R^3$ | A | $R^4$ | $R^5$ | $R^6$ | X | Y | Melting Point [°C.] |
|---|---|---|---|---|---|---|---|---|---|---|
| 16 | " | " | " | " | " | " | $-CH_2-COOCH_3$ | " | " | 106-8 |
| 17 | " | " | " | " | " | " | $-CH_2-$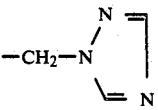 | " | " | 138-43 |
| 18 | " | " | " | " | " | " | 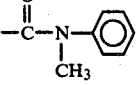 | " | " | RESIN |
| 19 | " | " | " | " | " | " | 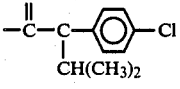 | " | " | 130-8 |
| 20 | " | " | " | " | " | " | $-\overset{O}{\underset{\|}{C}}-CH_3$ | " | " | 97-8 |
| 21 | " | " | " | " | " | " | $-\overset{O}{\underset{\|}{C}}-C(CH(CH_3)_2)-$C6H4-Cl | " | " | Oil |
| 22 | " | " | " | " | " | " | $-\overset{O}{\underset{\|}{C}}-O-C_2H_5$ | " | " | " |
| 23 | " | " | " | " | " | " | $-SO_2CH_3$ | " | " | " |
| 24 | " | " | " | " | " | " | 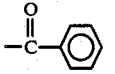 | " | " | " |
| 25 | " | " | " | N | — | " | H | " | " | 215-20 |
| 26 | " | " | " | " | — | " | $-CH_3$ | " | " | Oil |
| 27 | " | $-CH=CH=CH=CH-$ | | " | — | " | H | " | " | " |
| 28 | " | H | H | " | — | " | $-\overset{O}{\underset{\|}{C}}-C_6H_5$ | " | " | " |
| 29[2] | " | " | $CH_3$ | $C-R^4$ | H | " | H | " | " | 190-210 |
| 30[2] | Cl | " | Cl | " | " | $CH_3$ | " | " | " | |
| 31 | H | " | H | " | " | H | " | " | $-CH_2-CH(CH_3)_2$ | 148-50 |
| 32 | " | " | " | " | " | " | $-\overset{O}{\underset{\|}{C}}-CH_3$ | " | " | 75-8 |
| 33[2] | $NO_2$ | " | " | " | " | $C_2H_5$ | H | $CH_3$ | " | Oil |
| 34 | Cl | Cl | Cl | " | Cl | " | $-\overset{O}{\underset{\|}{C}}-N(CH_3)_2$ | " | " | " |

TABLE 1-continued

Compounds of the general formula I

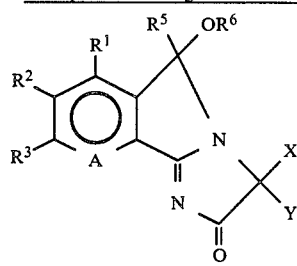

| Example No. | R¹ | R² | R³ | A | R⁴ | R⁵ | R⁶ | X | Y | Melting Point [°C.] |
|---|---|---|---|---|---|---|---|---|---|---|
| 35 | H | —CH=CH=CH=CH— | | " | H | " | $-\underset{\underset{O}{\overset{O}{\|}}}{\overset{\|}{S}}-\text{C}_6\text{H}_4-\text{CH}_3$ | " | " | Resin |
| 36 | " | H | H | " | " | H | H | —CH₂—CH₂—CH₂—CH₂—CH(CH₃)— | | 180-94 |
| 37 | " | " | " | N | — | " | —COCH₃ | CH₃ | CH(CH₃)₂ | Oil |
| 38 | " | " | " | " | — | " | —CO—Phenyl | " | " | |
| 39 | " | " | " | " | — | " | CONHCH₃ | " | " | |
| 40[2] | " | " | CH₃ | CR⁴ | H | " | H | " | cyclopropyl | |
| 41[2] | " | " | " | " | " | " | SO₂CF₃ | " | " | |
| 42[2] | " | " | " | " | " | " | COCCl₃ | " | " | |
| 43[2] | " | " | " | " | " | " | —CH₂—CON(morpholine dimethyl) | " | " | |
| 44[2] | " | " | " | " | " | " | CON(piperidine) | " | " | |
| 45[2] | " | " | " | " | " | " | CONH—Phenyl | " | " | |
| 46 | " | " | H | C—R⁴ | " | CH₃ | H | " | —CH(CH₃)₂ | 194-7 |
| 47 | " | " | " | N | — | H | COCH₃ | " | " | 113-5 |
| 48 | " | " | " | C—R⁴ | H | " | COOPhenyl | " | " | Oil |
| 49 | " | " | " | " | " | " | CONH—Phenyl | " | " | 178-80 |
| 50[2] | CH₃ | " | " | " | " | " | H | " | " | 166-74 |
| 51 | H | Cl | Cl | " | " | " | H | " | " | |
| 52 | " | Cl | " | " | " | " | COCH₃ | " | " | |
| 53[2] | " | H | CH₃ | " | " | " | CH₃ | " | " | Oil |
| 54[2] | " | " | " | " | " | " | COCH₃ | " | " | Oil |
| 55[2] | " | " | " | " | " | " | CO—Phenyl | " | " | Oil |

[1]formed in the preparation of 15 by partial isomerization
[2]Position isomer mixture (c.f. page 7)

B. BIOLOGICAL EXAMPLES

Test for herbicidal action

Damage to the weeds and tolerance by the crop plants was rated with a code from 0 to 5.
In this code,
0=no action (damage)
1=0-20% action
2=20-40% action
3=40-60% action
4=60-80% action
5=80-100% action

1. Action against weeds

Seeds or pieces of rhizome of monocotyledon and dicotyledon weeds were placed in loam soil in plastic pots (0 9 cm) and covered with soil. The compounds according to the invention, formulated as wettable powders or as emulsion concentrates, were applied to the surface of the soil in the form of aqueous suspensions or emulsions. The amount of water applied per pot corresponded, when converted, to 600 l/ha. After the treatment, the test pots were placed in a greenhouse and the test plants were grown under good growing conditions (temperature: 23°±1° C.; relative atmospheric humidity 60-80%). After about 3 weeks, the damage to the plants was rated visually. Untreated controls served as a comparison.

The compounds according to the invention exhibited a herbicidal activity, which in some cases was excellent, against economically important monocotyledon and dicotyledon harmful plants (c.f. Table 1).

In a similar manner, various weeds were grown to the 3-6 leaf stage in pots in a greenhouse and then treated with the compounds according to the invention (formulated as wettable powders) by the post-emergence method. 4 weeks later, the test plants were rated visually in comparison with untreated control plants by estimating the damage.

The compounds according to the invention also proved to be particularly effective in this test (c.f. Table 2).

TABLE 1

Herbicidal action of the novel compounds according to the invention in the pre-emergence method

| Example No. | Dose (kg a.i./ha) | Herbicidal Activity | | | |
|---|---|---|---|---|---|
| | | STM | SIA | ECG | LOM |
| 1 | 2,5 | 5 | 5 | 5 | 5 |
| 2 | 2,5 | 5 | 5 | 2 | 2 |
| 3 | 2,5 | 5 | 5 | 5 | 5 |
| 10 | 2,5 | 5 | 5 | 4 | 4 |
| 18 | 2,5 | 5 | 5 | 2 | 1 |
| 20 | 2,5 | 5 | 5 | 5 | 5 |
| 21 | 2,5 | 4 | 5 | 1 | 2 |
| 22 | 2,5 | 4 | 5 | 2 | 4 |
| 25 | 2,5 | 5 | 5 | 5 | 5 |
| 29 | 2,5 | 5 | 5 | 5 | 5 |
| 37 | 2,5 | 5 | 5 | 5 | 4 |
| 46 | 2,5 | 5 | 5 | 4 | 4 |
| 47 | 2,5 | 5 | 5 | 1 | 5 |
| 48 | 2,5 | 5 | 5 | 5 | 4 |
| 54 | 2,5 | 5 | 5 | 4 | 3 |

Abbreviations:
STM = *Stellaria media*
SIA = *Sinapis arvensis*
LOM = *Lolium multiflorum*
ECG = *Echinochloa crus galli*
a.i. = active ingredient

TABLE 2

Herbicidal action of the novel compounds according to the invention by the post-emergence method

| Example No. | Dose (kg a.i./ha) | Herbicidal Activity | | | |
|---|---|---|---|---|---|
| | | STM | SIA | ECG | LOM |
| 1 | 2,5 | 5 | 5 | 2 | 5 |
| 2 | 2,5 | 3 | 5 | 4 | 2 |
| 3 | 2,5 | 3 | 5 | 3 | 2 |
| 20 | 2,5 | 5 | 5 | 3 | 5 |
| 25 | 2,5 | 5 | 5 | 5 | 5 |
| 29 | 2,5 | 4 | 5 | 4 | 5 |
| 37 | 2,5 | 5 | 5 | 4 | 5 |
| 46 | 2,5 | 4 | 5 | 2 | 2 |
| 47 | 2,5 | 4 | 5 | 1 | 1 |
| 54 | 2,5 | 2 | 5 | 3 | 3 |

Test for growth-regulating action

1. Inhibition of growth of cereals

In dish experiments in a greenhouse, young cereal plants (wheat, barley and rye) in the 3 leaf stage were sprayed until dripping wet with the compounds to be tested. When the untreated control plants had reached a growth height of about 55 cm, the additional growth of all the plants was measured and the inhibition of growth was calculated in % of the additional growth of the control plants. In addition, the phytotoxic action of the compounds was observed. When stating the inhibition of growth, 100% means that growth has stopped, and 0% denotes a growth corresponding to that of the untreated control plants.

2. Inhibition of growth of dwarf beans

Dwarf beans 10-15 cm high are sprayed with the active ingredient formulations until dripping wet. After 2 weeks, the additional growth is measured and the inhibition of growth in % of the additional growth of the control plants is calculated. The plants show clear inhibition of the longitudinal growth.

We claim:

1. A compound of the formula I

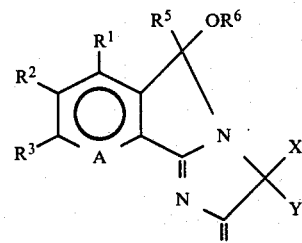

in which

A is N;

X is $C_1$-$C_4$-alkyl;

Y is $C_1$-$C_6$-alkyl, $C_3$-$C_6$-cycloalkyl, $C_2$-$C_4$-alkenyl, $C_2$-$C_4$-alkynyl, phenyl or benzyl;

$R^1$, $R^2$ and $R^3$ independently of one another are hydrogen, $C_1$-$C_4$ alkyl, $C_1$-$C_6$-alkoxy, $C_1$-$C_6$-alkoxycarbonyl, halogen, nitro, cyano, phenoxy, or $C_1$-$C_2$-halogenoalkyl;

$R^5$ is hydrogen or $C_1$-$C_6$-alkyl;

$R^6$ is hydrogen or $C_1$-$C_{12}$-alkyl, which is unsubstituted or mono- or di-substituted by $C_1$-$C_4$-alkoxy, $C_1$-$C_4$-alkoxyethoxy, $C_3$-$C_6$-cycloalkyl, benzyloxy, phenyl, tolyl, halogenophenyl, halogen, cyano, hydroxyl, $C_1$-$C_4$-alkoxycarbonyl, oxiranyl, tetrahydrofuryl, $C_1$-$C_4$-alkylamino, $C_1$-$C_4$-dialkylamino, $C_1$-$C_4$-alkylthio, triazolyl, imidazolyl or the grouping

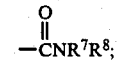

or is $C_3$-$C_6$-alkenyl, $C_3$-$C_6$-alkadienyl, $C_3$-$C_6$-halogenoalkenyl, $C_3$-$C_6$-cycloalkyl, $C_5$- or $C_6$-cycloalkenyl or $C_3$-$C_6$-alkynyl; or is phenyl, which is unsubstituted or substituted by up to two $C_1$-$C_4$-alkyl, nitro, $C_1$-$C_4$-alkoxycarbonyl, halogen or methoxy groups; or is $C_1$-$C_6$-alkoxycarbonyl, phenoxycarbonyl, halogenophenoxycarbonyl, $C_1$-$C_4$-alkylsulfonyl, trihalogenomethysulfonyl, benzenesulfonyl, halogenobenzenesulfonyl, toluenesulfonyl or the grouping

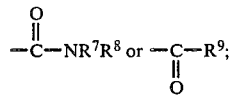

R[7] is hydrogen or $C_1$–$C_4$-alkyl; and

R[8] is hydrogen, $C_1$–$C_6$-alkyl, $C_3$–$C_6$-alkenyl, phenyl, halogenophenyl or methylphenyl; or R[7] and R[8] together with the nitrogen atom, form a pyrrolidine, piperdine, morpholine or N-methylpiperazine ring which is unsubstituted or substituted by up to two methyl groups; and R[9] is $C_1$–$C_{12}$-alkyl, unsubstituted or mono-, di or tri-substituted by fluorine, chlorine and bromine and may be further monosubstituted by $C_1$–$C_4$-alkoxy, $C_1$–$C_4$-alkoxycarbonyl, $C_1$–$C_4$-alkylthio, phenyl or phenoxy, the phenyl or phenoxy being unsubstituted or mono-, di- or tri-substituted by halogen, $C_1$–$C_4$-alkyl, $NO_2$, $CF_3$ or $C_1$–$C_4$-alkoxy; or is $C_2$–$C_6$-alkenyl, $C_3$–$C_6$-halogenoalkenyl, $C_3$–$C_6$-alkynyl or phenyl, which is unsubstituted or mono- or di-substituted by F, Cl, Br, $CF_3$, $C_1$–$C_4$ alkyl or $C_1$–$C_4$-alkoxy, and optical isomers thereof and the acid addition salts and N-oxides.

2. The compound as claimed in claim 1 in which R[6] is $C_1$–$C_{12}$-alkyl, which is monosubstituted by $C_1$–$C_4$-alkoxy, $C_1$–$C_4$alkoxyethoxy, $C_3$–$C_6$-cycloalkyl, benzyloxy, phenyl, tolyl, halogenophenyl, halogen, cyano, hydroxyl, $C_1$–$C_4$-alkoxycarbonyl, oxiranyl, tetrahydrofuryl, $C_1$–$C_4$-alkylamino, $C_1$–$C_4$-dialkylamino, $C_1$–$C_4$-alkylthio, triazolyl, imidazolyl or the grouping

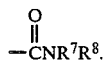

3. The compound as claimed in claim 1 in which —NR[7]R[8] is a pyrrolidine, piperidine or N-methyl-piperazine ring.

4. The compound as claimed in claim 1 in which R[1], R[2], R[3] and R[5] are H; R[6] is H, $CH_3$ $COC_6H_5$, $COCH_3$ or $CONHCH_3$; X is $CH_3$ and Y is $CH(CH_3)_2$.

5. The compound as claimed in claim 1 in which R[7] and R[8] together with the nitrogen atom form a piperidine ring.

6. A compound as in claim 1 which is

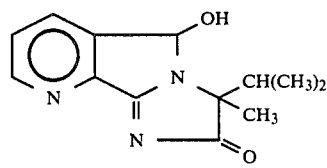

(25)

7. A compound as in claim 1 which is

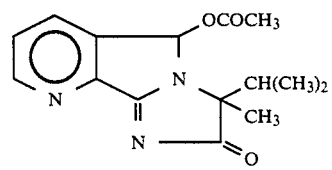

(37)

8. A herbicidal or growth-regulating agent, which comprises as the active ingredient, a compound according to claim 1 in association with an acceptable carrier.

9. A method of combating undesired plants or for regulating growth, which comprises applying an effective amount of a compound as claimed in claim 1 to the cultivation area to be treated or to the plants to be treated.

* * * * *